(12) United States Patent
Conover (10) Patent No.: US 7,402,724 B2
(45) Date of Patent: Jul. 22, 2008

(54) LONGEVITY AND PAPP-A

(75) Inventor: Cheryl A. Conover, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 58 days.

(21) Appl. No.: 11/093,555

(22) Filed: Mar. 30, 2005

(65) Prior Publication Data

US 2005/0232863 A1 Oct. 20, 2005

Related U.S. Application Data

(63) Continuation-in-part of application No. 10/499,472, filed as application No. PCT/US03/00115 on Jan. 3, 2003, now Pat. No. 7,220,892.

(60) Provisional application No. 60/345,709, filed on Jan. 4, 2002.

(51) Int. Cl.
*G01N 33/00* (2006.01)
*A01K 67/027* (2006.01)

(52) U.S. Cl. .................. 800/3; 800/14; 800/18

(58) Field of Classification Search ............ None
See application file for complete search history.

(56) References Cited

U.S. PATENT DOCUMENTS

| | | | |
|---|---|---|---|
| 5,849,991 | A | 12/1998 | D'Apice et al. |
| 6,177,610 | B1 | 1/2001 | Lee et al. |
| 2002/0102252 | A1 | 8/2002 | Gu et al. |

OTHER PUBLICATIONS

Harrison, SJ et al, 2002, Efficient generation of alpha(1,3) galactosyltransferase knockout porcine fetal fibroblasts for nuclear transfer, Transgenic Research, 11:143-150, 2002.*
Thomson AJ et al., 2003, Gene targeting in livestock, Reprod. Supp., 61:495-508.*
Wang, B et al. 2003, Specific genetic modifications of domezstic animal by gene targeting and animal cloning, Reproductive biology and endocrinology, 1:103.*
Wolfer, DP et al, 2002, Knockout mice: simple solutions to the problems of genetic background and flanking genes, Trends in Neurosciences, 25:336-340.*
Holzenberger M. et al., 2004, IGF-1 signaling and aging, Experimental Gerontology, 39:1761-1764.*
Moreadith, 1997, Gene targeting in embryonic stem cells : the new physiology and metabolism, Journal of Molecular Medicine, vol. 75, pp. 208-216.*
Mullins, 1996, J. Clin. Invest., vol. 98, pp. S37-S40.*
Coschigano, K et al., 2003, Endocrinology, 144:3799-3810.*
Branch, A., 1998, A good antisense is hard to find, TIBS, 23:45-50.*
Soe, R et al, 2002, FEBS, 269:2247-2256.*
Agrawal S et al., 2000, Antisense therapeutics, is it as simple as complementary base recognition?, Molec Med Today, 6:72-81.*
GenBank Accession No. AF258461 dated Sep. 2, 2000.

GenBank Accession No. X68280 dated Dec. 16, 1993.
Adams et al., "Developmental patterns of insulin-like growth factor-I and -II synthesis and regulation in rat fibroblasts," *Nature*, 1983, 302:150-153.
Baker et al., "Role of Insulin-like Growth Factors in Embryonic and Postnatal Growth," *Cell*, 1993, 75:73-82.
Boldt et al., "Mutational analysis of the proteolytic domain of pregnancy-associated plasma protein-A (PAPP-A): classification as a metzincin," *Biochem. J.*, 2001, 358:359-367.
Breslow, "Mouse Models of Atherosclerosis," *Science*, 1996, 272:685-688.
Burns and Hassan, "Cell survival and proliferation are modified by insulin-like growth factor 2 between days 9 and 10 of mouse gestation," *Development*, 2001, 128:3819-3830.
Cibelli et al., "Cloned Transgenic Calves Produced from Nonquiescent Fetal Fibroblasts," *Science*, 1998, 280:1256-1258.
Clemmons, "Insulin-like Growth Factor Binding Proteins and their Role in Controlling IGF Actions," *Cytokine Growth Factor Rev.*, 1977, 8(1):45-62.
Conover et al., "Cleavage Analysis of Insulin-like Growth Factor (IGF)-dependent IGF-binding Protein-4 Proteolysis and Expression of Protease-resistant IGF-binding Protein-4 Mutants," *J. Biol. Chem.*, 1995, 270(9):4395-4400.
DeChiara et al., "A growth-deficiency phenotype in heterozygous mice carrying an insulin-like growth factor II gene disrupted by targeting," *Nature*, 1990, 345:78-80.
Fowlkes, "Insulin-like Growth Factor-Binding Protein Proteolysis. An Emerging Paradigm in Insulin-like Growth Factor Physiology," *Trends Endocrinol. Metab.*, 1997, 8(8):299-306.
Holzenberger et al., "IGF-1 receptor regulates lifespan and resistance to oxidative stress in mice," *Nature*, 2003, 421:182-187.
Lawrence et al., "The insulin-like growth factor (IGF)-dependent IGF binding protein-4 protease secreted by human fibroblasts is pregnancy-associated plasma protein-A," *Proc. Natl. Acad. Sci. USA*, 1999, 96:3149-3153.
Liu et al., "Mice Carrying Null Mutations of the Genes Encoding Insulin-like Growth Factor 1 (*Igf-1*) and Type 1 IGF Receptor (*Igf1r*)," *Cell*, 1993, 75:59-72.
Ludwig et al., "Mouse Mutants Lacking the Type 2 IGF Receptor (IGF2R) Are Rescued from Perinatal Lethality in *Igf2* and *Igf1r* Null Backgrounds," *Dev. Biol.*, 1996, 177(2):517-535.
Nakashima et al., "ApoE-Deficient Mice Develop Lesions of All Phases of Atherosclerosis Throughout the Arterial Tree," *Arterioscler. Thromb.*, 1994, 14(1):133-140.

(Continued)

*Primary Examiner*—Valarie Bertoglio
(74) *Attorney, Agent, or Firm*—Fish & Richardson P.C.

(57) ABSTRACT

This document provides materials and methods related to PAPP-A polypeptides, aging, and transgenic non-human mammals whose genomes comprise a disrupted PAPP-A allele. Methods for making such transgenic non-human mammals, and using them and other mammals to identify and characterize agents that affect conditions related to PAPP-A activity, such as vascular restenosis, atherosclerosis, wound healing, cancer, fibrosis, bone development, fetal development, longevity, and fracture repair, also are provided.

7 Claims, 3 Drawing Sheets

OTHER PUBLICATIONS

Orban et al., "Tissue- and site-specific DNA recombination in transgenic mice," *Proc. Natl. Acad. Sci. USA*, 1992, 89(15):6861-6865.

Overgaard et al., "Expression of Recombinant Human Pregnancy-associated Plasma Protein-A and Identification of the Proform of Eosinophil Major Basic Protein as Its Physiological Inhibitor," *J. Biol. Chem.*, 2000, 275(40):31128-31133.

Plump et al., "Severe Hypercholesterolemia and Atherosclerosis in Apolipoprotein E-Deficient Mice Created by Homologous Recombination in ES Cells," *Cell*, 1992, 71(2):343-353.

Qin et al., "Evidence That the Interaction between Insulin-like Growth Factor (IGF)-II and IGF Binding Protein (IGFBP)-4 Is Essential for the Action of the IGF-II-Dependent IGFBP-4 Protease," *Arch. Biochem. Biophys.*, 2000, 379(2):209-216.

Shastry, "Gene disruption in mice: Models of development and disease," *Mol. Cell. Biochem.*, 1998, 181:163-179.

Smith et al., "Development: Early-pregnancy origins of low birth weight," *Nature*, 2002, 417:196.

Stewart and Rotwein, "Growth, Differentiation, and Survival: Multiple Physiological Functions for Insulin-Like Growth Factors," *Physiol. Rev.*, 1996, 76(4):1005-1026.

Vallette et al., "Construction of mutant and Chimeric genes using the polymerase chain reaction," *Nucl. Acids Res.*, 1989, 17(2):723-733.

Wakayama et al., "Full-term development of mice from enucleated oocytes injected with cumulus cell nuclei," *Nature*, 1998, 394(6691):369-374.

Wilmut et al., "Viable offspring derived from fetal and adult mammalian cells," *Nature*, 1997, 385(6619):810-813.

Zaina et al., "Insulin-like Growth Factor II Plays a Central Role in Atherosclerosis in a Mouse Model," *J. Biol. Chem.*, 2002, 277(6):4505-4511.

Zhang et al., "Spontaneous Hypercholesterolemia and Arterial Lesions in Mice Lacking Apolipoprotein E," *Science*, 1992, 258:468-471.

Mazerbourg, S., et al., Pregnancy-Associated Plasma Protein-A (PAPP-A) in Ovine, Bovine, Porcine, and Equine Ovarian Follicles: Involvement in IGF Binding Protein-4 Proteolytic Degraation and MRNA Expression During Follicular Development, *Endocrinology*, 142(12):5243-5253, 2001.

Griffiths et al., "Current Concepts of PLP and Its Role in the Nervous System," *Microscopy Research and Technique*, 1998, 41:344-348.

Leonard et al., "Role of the Common Cytokine Receptor γ Chain in Cytokine Signaling and Lymphoid Development," *Immunol. Rev.*, 1995, 148:97-114.

\* cited by examiner

LONGEVITY AND PAPP-A

CROSS-REFERENCE TO RELATED APPLICATIONS

This application is a continuation-in-part of U.S. application Ser. No. 10/499,472, A filed Sep. 16, 2004, now. U.S. Pat. No. 7,220,892, which is a National Stage application under 35 U.S.C. §371 that claims the benefit of PCT/US03/00115, filed Jan. 3, 2003, which claims the benefit of U.S. Provisional Application Ser. No. 60/345,709, filed Jan. 4, 2002.

TECHNICAL FIELD

This document involves methods and materials related to making and using transgenic rodents with genomic disruptions affecting the expression of pregnancy-associated plasma protein-A (PAPP-A). This document also involves methods and materials related aging.

BACKGROUND

The insulin-like growth factors (IGF-I and -II) are important determinants of fetal growth and postnatal development. Baker, J., et al. *Cell* 75, 73-82 (1993); and Stewart, C. E. H., and Rotwein, P. *Physiol. Rev.* 76, 1005-1026 (1996). IGF bioactivity is modulated by IGF binding proteins (IGFBPs), which, in turn, are regulated by specific proteases. Clemmons, D. R. *Cytokine Growth Factor Rev.* 8, 45-62 (1977); and Fowlkes, J. L. *Trends Endocrinol. Metab.* 8, 299-306 (1997).

PAPP-A increases IGF bioavailability and mitogenic effectiveness in vitro through regulated cleavage of IGFBP-4. PAPP-A is a large placental glycoprotein, present in the serum of pregnant women in increasing concentrations throughout pregnancy. PAPP-A in pregnancy serum is linked via a disulfide bond to the proform of eosinophil major basic protein (proMBP), forming an approximately 500 kDa 2:2 complex, denoted PAPP-A/proMBP. The serum form of PAPP-A is derived from a pre-proprotein containing a putative 22-residue signal peptide, a pro-part of 58 residues, and a 1547-residue circulating mature polypeptide. The amino acid sequence shows no global similarity to any known protein, but it contains two sequence motifs common to the metzincins, a superfamily of metalloproteases, three Lin-12/Notch repeats known from the Notch protein superfamily, and five short consensus repeats known from components of the complement system. Free PAPP-A cannot be isolated from pregnancy serum, but can be isolated in conditioned media from human fibroblasts.

The PAPP-A/proMBP complex is absent from maternal serum in pregnancies where the mother is carrying a fetus with Cornelia de Lange syndrome. Recently, PAPP-A and proMBP in conjunction with SP1 have been shown to be effective markers for detecting fetuses affected with Down's syndrome in weeks 7-12 of gestation.

SUMMARY

This document is based, in part, on the discovery that transgenic mice whose genomes contain a disruption in a nucleic acid encoding a PAPP-A polypeptide are born as proportional dwarfs. Homozygous mutants are 40% smaller than their wild-type or heterozygous littermates and maintain this size difference during post-natal growth. The impact of the mutation is exerted in early embryogenesis. Although PAPP-A null mice normally express IGF-II and IGFBP-4, they are completely devoid of IGFBP-4 proteolytic activity. These results implicate PAPP-A as a critical modulator of IGF-II signaling during mammalian development. As a result, such transgenic mice provide a model to study the biological role of PAPP-A in such diverse systems as wound healing, bone remodeling, cancer, atherosclerosis, fetal development, longevity, and follicular development.

This document is also based, in part, on the confirmation that reducing PAPP-A polypeptide activity increases a mammal's lifespan. Both male and female transgenic mice whose genomes contain a disruption in a nucleic acid encoding a PAPP-A polypeptide exhibit a 30 to 40 percent increase in lifetime survival as compared to wild-type controls. This document provides methods and materials that can be used to increase a mammal's lifespan. This document also provides methods and materials that can be used to identify compounds having the ability to increase a mammal's lifespan. Identifying compounds having the ability to increase a mammal's lifespan can allow mammal to live longer, more productive lives.

In one aspect, this document provides a transgenic rodent whose genome includes a disruption of an endogenous PAPP-A gene, wherein the disruption results in the transgenic rodent having a reduced weight relative to a corresponding control rodent. The transgenic rodent can be a mouse. The disruption can be heterozygous. Alternatively, the disruption can be homozygous. Further, the disruption can affect an exon within the endogenous PAPP-A gene (e.g., exon 4). The corresponding control rodent can be a wild-type rodent. Alternatively, the genome of the corresponding control rodent can include a heterozygous disruption in the endogenous PAPP-A gene. The transgenic rodent further can be deficient in Apolipoprotein E. This document also provides progeny of such transgenic rodents. This document further provides cells isolated from such transgenic rodents.

In another aspect, this document provides a nucleic acid vector including a PAPP-A polynucleotide, wherein the PAPP-A polynucleotide is disrupted by a marker polynucleotide. This document also provides a nucleic acid vector including a PAPP-A polynucleotide lacking exon 4.

In another aspect, this document features a method for identifying a compound having the ability to increase a mammal's lifespan. The method includes (a) administering a test compound having the ability to reduce PAPP-A polypeptide activity to a population of mammals, and (b) determining whether or not the population has a longer average lifespan than the average lifespan of a control population not administered the test compound, wherein the presence of the longer average lifespan indicates that the test compound is the compound having the ability to increase a mammal's lifespan. The population of mammals can be a population of mice. The test compound can be an siRNA molecule. The method can include comparing the average lifespan of the population of mammals to the average lifespan of a positive control population of mammals. The positive control population of mammals can be a population of rodents whose genome contains a disruption of an endogenous PAPP-A gene. The method can include determining whether or not the population has at least a 10 percent longer average lifespan than the average lifespan of a control population not administered the test compound. The method can include determining whether or not the population has at least a 20 percent longer average lifespan than the average lifespan of a control population not administered the test compound. The method can include determining whether or not the population has at least a 30 percent longer average lifespan than the average lifespan of a control population not administered the test compound. The method can include determining whether or not the population has at least a 40 percent longer average lifespan than the average lifespan of a control population not administered the test compound. The method can include determining whether or not the population has a 30 to 40 percent longer average lifespan than the average lifespan of a control population not administered the test compound. The method can include, prior to step (a), determining whether or not a compound is a test compound having the ability to reduce PAPP-A polypeptide activity.

In another aspect, this document features a population of mice, wherein each mouse is older than 900 days and exhibited reduced PAPP-A polypeptide activity. The genome of each mouse can contain a disruption of an endogenous PAPP-A gene. Each mouse can be older than 950 days, older than 1000 days, or older than 1050 days.

In another aspect, this document features a plurality of non-human mammals that are at least 10 percent older than the average lifespan for the species of the non-human mammals and that exhibited reduced PAPP-A polypeptide activity. The genome of each non-human mammal of the plurality can contain a disruption of an endogenous PAPP-A gene. Each non-human mammal of the plurality can be at least 20 percent older than the average lifespan. Each non-human mammal of the plurality can be at least 30 percent older than the average lifespan. Each non-human mammal of the plurality can be between 30 and 40 percent older than the average lifespan.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

This document is based, in part, on the discovery that a transgenic mouse whose genome contains a disruption in a nucleic acid encoding a PAPP-A polypeptide exhibits a reduced weight compared to that of a control mouse. This reduced weight is first observed at birth and persists during development of the transgenic mouse. Since the transgenic mouse is fertile and can produce viable offspring, it provides a valuable model for determining the role of PAPP-A in growth-promoting, non-pregnant states, such as vascular restenosis, atherosclerosis, wound healing, fibrosis, bone development, longevity, and fracture repair, as well as pregnancy related conditions such as fetal development and risk for low birth weights in offspring.

Nucleic Acid Constructs

The nucleic acid constructs provided herein can include a disrupted PAPP-A polynucleotide. As used herein, "disrupted PAPP-A polynucleotide" refers to a modification in the PAPP-A polynucleotide such that the expression of functional PAPP-A polypeptide is reduced or prevented. Modifications that can result in a disrupted PAPP-A polynucleotide include, without limitation, insertions, deletions, substitutions, and combinations thereof. Modifications can be made in any region of a PAPP-A polynucleotide, including, introns, exons, promoter, or 5'- or 3'-untranslated regions. For example, a PAPP-A polynucleotide can include a substitution within an exon, resulting in a disruption of PAPP-A expression. Suitable exons can include any of the 22 PAPP-A exons. For example, exon 4 can be modified such that PAPP-A protease activity is ablated, or PAPP-A expression is disrupted. Exon 4 of the mouse PAPP-A gene contains the conserved zinc binding and Met-turn consensus in metzincins. PAPP-A polynucleotides suitable for the methods and materials provided herein include, without limitation, those described in GenBank accession numbers AF258461 and X68280.

Specific modifications such as point mutations can be introduced into the polynucleotide by, for example, oligonucleotide-directed mutagenesis. In this method, a desired change is incorporated into an oligonucleotide, which then is hybridized to the polynucleotide. The oligonucleotide is extended with a DNA polymerase, creating a heteroduplex that contains a mismatch at the introduced point change, and a single-stranded nick at the 5' end, which is sealed by a DNA ligase. The mismatch is repaired upon transformation of *E. coli*, and the modified polynucleotide encoding the corresponding modified polypeptide can be re-isolated from *E. coli*. Kits for introducing site-directed mutations can be purchased commercially. For example, Muta-Gene® in-vitro mutagenesis kits can be purchased from Bio-Rad Laboratories, Inc. (Hercules, Calif.).

PCR techniques also can be used to introduce modifications to a polynucleotide. See, for example, Vallette et al., *Nucleic Acids Res.*, 1989, 17(2):723-733. PCR refers to a procedure or technique in which target nucleic acids are amplified. Sequence information from the ends of a region of interest or beyond typically is employed to design oligonucleotide primers that are identical in sequence to opposite strands of the template to be amplified, whereas for introduction of modifications, oligonucleotide primers that incorporate the desired modification are used to amplify the polynucleotide. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example, in *PCR Primer: A Laboratory Manual*, Ed. by Dieffenbach, C. and Dveksler, G., Cold Spring Harbor Laboratory Press, 1995.

PAPP-A polynucleotides encoding modified polypeptides also can be produced by chemical synthesis, either as a single polynucleotide molecule or as a series of polynucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed.

DNA polymerase is used to extend the oligonucleotides, resulting in a double-stranded nucleic acid molecule per oligonucleotide pair, which then can be ligated into a vector.

Suitable nucleic acid constructs are amenable to genomic integration by homologous recombination. Suitable vectors for genomic integration by homologous recombination include, without limitation, pKO Scrambler, pMC1neo, and pMC1-hsv-tk, all from Stratagene (La Jolla, Calif.).

Typically, a nucleic acid construct provided herein includes a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3' phosphotransferase gene that imparts resistance to geneticin (G418, an aminoglycoside antibiotic) or neomycin, and other antibiotic resistance markers, such as the hygromycin-B-phosphotransferase gene that imparts hygromycin resistance. Other selection systems include negative-selection markers such as the thymidine kinase (TK) gene from herpes simplex virus. Nucleic acid constructs utilizing both positive and negative drug selection also can be used. For example, a construct can contain the aminoglycoside phosphotransferase gene and the TK gene. In this system, cells are selected that are resistant to G418 and sensitive to gancyclovir.

Transgenic Non-Human Mammals

The transgenic non-human mammals provided herein can include a disrupted PAPP-A polynucleotide. In addition, progeny and cells of such non-human mammals can be obtained and used as described herein. Non-human mammals include, for example, rodents such as rats, guinea pigs, and mice, and farm animals such as pigs, sheep, goats, horses, and cattle. Homologous recombination can be used to disrupt an endogenous PAPP-A polynucleotide in a transgenic non-human mammal provided herein. See, Shastry, B. S., *Mol. Cell Biochem.*, (1998) 181(1-2):163-179, for a review of gene targeting technology. In addition, Cre/lox technology can be used to generate transgenic non-human mammals with conditional PAPP-A gene deletions. See, Orban, P. C., et al., *Proc. Natl. Acad. Sci.* (1992) 89 (15): 6861-6865, for a review of Cre/lox technology.

To create transgenic non-human mammals having a particular gene inactivated in all cells, it is necessary to introduce a construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced construct in all its somatic and germ cells because the zygote is the mitotic progenitor of all cells in the embryo. Since targeted insertion of a construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals with a disrupted endogenous PAPP-A nucleic acid. That is, cultured ES cells can be transformed with a PAPP-A nucleic acid construct and cells selected in which the PAPP-A gene is disrupted.

Nucleic acid constructs can be introduced into ES cells, for example, by electroporation or other standard technique. Selected cells can be screened for gene targeting events. For example, the polymerase chain reaction (PCR) can be used to confirm the presence of the nucleic acid construct.

The ES cells further can be characterized to determine the number of targeting events. For example, genomic DNA can be harvested from ES cells and used for Southern analysis. See, for example, Section 9.37-9.52 of Sambrook et al., "Molecular Cloning, A Laboratory Manual", second edition, Cold Spring Harbor Press, Plainview; N.Y., 1989.

To generate a transgenic non-human mammal, ES cells having at least one inactivated PAPP-A allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain progeny, whose cells (including germ cells) carry the inactivated PAPP-A allele. If the original ES cell was heterozygous for the inactivated PAPP-A allele, several of these progeny can be bred with each other in order to generate progeny homozygous for the inactivated allele.

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with constructs, it is useful to incorporate at least about 8 kb of homologous DNA into the targeting construct. In addition, it is also useful to prepare the constructs from isogenic DNA.

Embryos derived from microinjected eggs can be screened for homologous recombination events in several ways. For example, if a PAPP-A allele is interrupted by a coding region that produces a detectable (e.g., fluorescent) expression product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate transgenic non-human mammals. For example, fetal fibroblasts can be genetically modified such that they contain an inactivated endogenous PAPP-A allele thereby preventing PAPP-A expression, and then fused with enucleated oocytes. After activation of the oocytes, the eggs are cultured to the blastocyst stage, and implanted into a recipient. See, Cibelli, J. B. et al., *Science*, (1998) 280:1256-1258. Adult somatic cells, including, for example, cumulus cells and mammary cells, can be used to produce animals such as mice and sheep, respectively. See, for example, Wakayama, T. et al., *Nature*, (1998) 394(6691):369-374; and Wilmut, I. et al., *Nature*, (1997) 385(6619):810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama, T. et al., 1998, supra. Transgenic non-human mammals heterozygous for a disrupted endogenous PAPP-A allele can be mated to produce homozygous non-human mammals.

Genotype

A transgenic non-human mammal provided herein can be either heterozygous or homozygous for a disrupted PAPP-A allele. Initial screening to determine whether a genome comprises a PAPP-A nucleic acid construct can be accomplished by Southern blot analysis or PCR techniques. See, for example, sections 9.37-9.52 of Sambrook et al., 1989, "*Molecular Cloning, A Laboratory Manual*", second edition, Cold Spring Harbor Press, Plainview, N.Y., for a description of Southern analysis. Further, endogenous PAPP-A mRNA expression levels in tissues from a transgenic non-human mammal can be assessed using techniques that include, but are not limited to, Northern blot analysis of tissue samples obtained from the mammal, in situ hybridization analysis, and reverse-transcriptase PCR (RT-PCR). For example, a sample such as tail tissue can be collected from a transgenic mouse whose genome is suspected to include a PAPP-A nucleic acid construct. Nucleic acid molecules (e.g., DNA) can be purified from the sample using a commercially available kit (e.g., the Qiagen DNeasy Tissue Kit). The purified nucleic acid molecules can be used to genotype the transgenic mouse, e.g., by hybridizing a labeled probe to the nucleic acid molecule and blotting or by amplifying portions of the PAPP-A nucleic acid construct. Amplified reaction products can be separated by gel electrophoresis, and, based on the presence or absence of genotyping bands, the transgenic mouse can be classified as non-transgenic, heterozygous, or homozygous. Segregation analysis of PCR products can be used to determine heterozygosity or homozygosity.

Phenotype

In addition to exhibiting a particular genotype, a transgenic non-human mammal provided herein also can exhibit one or more useful phenotypes. A transgenic mouse provided herein, for example, can exhibit a proportional reduction in weight or a developmental delay in bone development. It is understood that the presence of a particular phenotype is assessed by comparing that phenotype to the corresponding phenotype exhibited by a suitable control non-human mammal. Suitable control non-human mammals can include wild-type mammals or mammals heterozygous for a disruption in a PAPP-A allele. For example, the weight of a transgenic mouse homozygous for a disruption in both PAPP-A alleles can be compared to the weight of a control wild-type mouse or control heterozygous mouse of the same age. As described herein, the weight of a 6-week old mouse homozygous for a disrupted PAPP-A allele is significantly less than that of a wild-type or heterozygous control mouse. Typically, a difference in a phenotype is considered statistically significant at $p \leq 0.05$ with an appropriate parametric or non-parametric statistic, e.g., Chi-square test, Student's t-test, Mann-Whitney test, or F-test.

Using Transgenic Non-Human Mammals as Disease Models

Transgenic non-human mammals provided herein can be used as models for evaluating the role of PAPP-A activity in both pregnancy related and non-pregnancy related conditions (e.g., growth-promoting conditions), such as vascular restenosis, atherosclerosis, wound healing, fibrosis, bone development, low birth weights, fetal development, longevity, and fracture repair. For example, the role of PAPP-A activity in vascular restenosis after angioplasty can be evaluated in a transgenic mouse homozygous for a disruption in both PAPP-A alleles. In one embodiment, a series of transgenic mice each homozygous for a disruption in both PAPP-A alleles are subjected to angioplasty. Each transgenic mouse is then euthanized at a different time (e.g., at 1, 4, 7, 14, or 28 days) after angioplasty and the site of angioplasty is removed. The amount of neointimal formation is assessed in the removed site and compared to the amount of neointimal formation in an angioplasty site removed from a suitable control mouse (e.g., non-transgenic or heterozygous for a PAPP-A disruption). In PAPP-A deficient animals after vascular injury, there is no apparent neointimal formation compared with corresponding wild-type animals.

In other embodiments, the role of PAPP-A activity in atherosclerosis can be evaluated by cross-breeding transgenic non-human mammals that are homozygous for a disruption in both PAPP-A alleles with Apolipoprotein (Apo) E deficient animals (e.g., ApoE deficient mice). ApoE is a ligand important in lipoprotein clearance. Mice deficient in ApoE develop atherosclerotic lesions resembling those observed in humans in their site of predilection and progression with age. Atherosclerotic lesions in ApoE deficient mice are exacerbated when the mice are fed a high-cholesterol, high-fat, Western type diet. See e.g., Zhang et al., *Science* (1992) 258:468-471; and Breslow *Science* (1996) 272:685-688. ApoE deficient mice are commercially available (e.g., from Jackson Laboratory (Bar Harbor, Me.)). In particular, PAPP-A(−/−) mice can be cross-bred with apoE deficient mice, and transgenic mice deficient in both PAPP-A and ApoE can be selected. Such mice may be resistant to developing atherosclerosis.

Transgenic non-human animals that are deficient in PAPP-A also will allow the role of PAPP-A in regulating lifespan to be assessed. Experimental inactivation or down-regulation of IGF receptor signaling can increase lifespan in several species, including mice. See, Holzenberger et al., *Nature* (2002) December 4. Reduced circulating IGF-I levels, e.g., due to caloric restriction, also have been credited to increased lifespan in mice and humans. Transgenic non-human animals with a disruption in both PAPP-A alleles have decreased circulating levels of IGF-I and are proportional dwarfs, and as a result, are expected to have an increased lifespan. Such animals can be used in a variety of studies to assess longevity and to evaluate other components that may play a role in regulating lifespan.

Screening Compounds Using Transgenic Non-Human Mammals

The transgenic non-human mammals provided herein as well as other non-human mammals can be used to screen, for example, toxicity of compounds that are PAPP-A substrates, drugs that alter PAPP-A activity, or compounds that alter both pregnancy and non-pregnancy conditions related to PAPP-A activity, such as vascular restenosis, atherosclerosis, wound healing, fibrosis, bone development, low birth weights, fetal development, longevity, and fracture repair. For example, bone development can be assessed in a test mouse exhibiting PAPP-A activity in the presence of a test compound, and compared with bone development in a corresponding control transgenic mouse homozygous for a PAPP-A disruption in the presence of the same test compound. As used herein, suitable test compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of the test compound depends on the type of compound and in vitro test data desired.

As described herein, the methods and materials provided herein can be used to identify compounds having the ability to increase a mammal's lifespan. For example, a test compound can be administered to a population of mammals (e.g., mice, rats, monkeys, or humans) to assess its ability to increase lifespan. A test compound can be administered at any frequency and for any duration. For example, a test compound can be administered one, two, three, four, five, or more times on a daily, weekly, or monthly basis for a duration that is for one, two, three, four, five, or more weeks, months, or years. In some cases, a test compound can be administered beginning at some point after birth and extending until the mammal dies. The population of mammals to be treated can contain any number of mammals (e.g., 5, 10, 15, 20, 25, 50, or more mammals). In some embodiments, one or more control populations can be used. For example, a population of untreated, wild-type mammals can be used as a negative control, while a population of untreated mammals homozygous for a PAPP-A disruption can be used as a positive control.

As described herein, any type of compound can be used as a test compound. In some cases, a test compound can be a compound having the ability to reduce PAPP-A polypeptide activity. Such test compounds can be obtained using any method such as those in vitro and in vivo methods commonly used to identify protease inhibitors. For example, an in vitro colorimetric screen can be designed to assesses cleavage of a substrate (e.g., an IGF polypeptide) by PAPP-A polypeptides. In addition, any type of compound can be identified as having the ability to reduce PAPP-A polypeptide activity in vitro or in vivo. Examples of compounds having the ability to reduce PAPP-A polypeptide activity can include, without limitation, siRNA molecules designed to reduce expression of PAPP-A polypeptides, anti-PAPP-A antibodies, antisense oligonucleotides designed to reduce expression of PAPP-A polypeptides, and protease inhibitors (e.g., ProMBP, 1,10-phenanthroline, and EDTA). Once identified, the test compound having the ability to reduce PAPP-A polypeptide activity can be assessed for the ability to increase lifespan as described herein.

Mammals (e.g., transgenic non-human mammals) can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

The invention will be further described in the following examples, which do not limit the scope of the invention described in the claims.

EXAMPLES

Example 1

Generation of a PAPP-A Knockout Mouse

Figure 1:
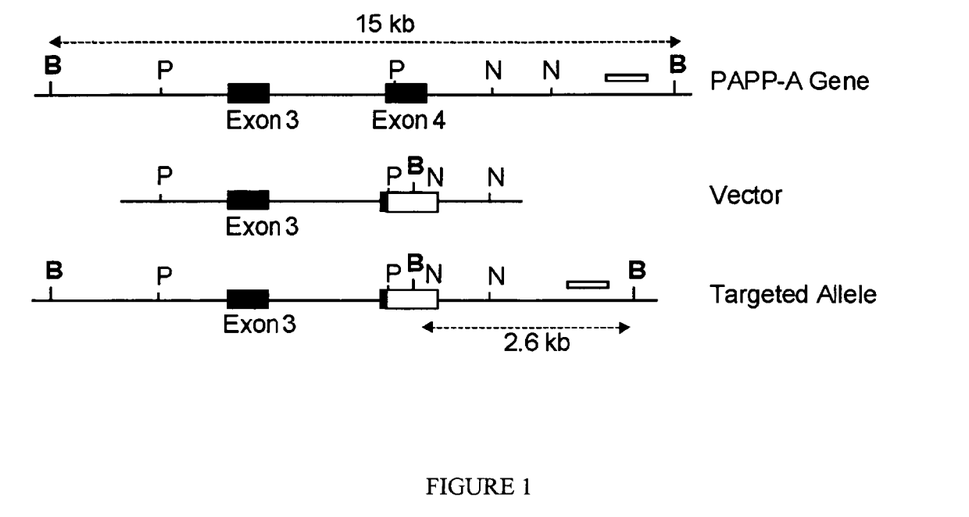
FIG. 1 is a schematic representation of the mouse gene in the region of exons 3 and 4 of the PAPP-A locus, the replacement vector, and the targeted allele.

A knockout construct was made using a portion of mouse genomic DNA encoding PAPP-A (FIG. 1). This portion included exon 4 of the PAPP-A gene. A pKO Scrambler vector (Stratagene, La Jolla, Calif.) was used for construction of the replacement vector. A neomycin-resistant gene (neo) cassette was used to replace 1.6 kb of PAPP-A gene sequence including most of exon 4, resulting in the neo cassette being flanked by a 6 kb PstI (P) fragment and a 2 kb NsiI (N) fragment of mouse PAPP-A locus DNA (5' and 3', respectively). Addition of neo also introduced a novel BamHI (B) restriction site. A cassette for thymidine kinase gene selection was located upstream of the first set of polylinker restriction sites. Linearized replacement vector DNA was introduced into 129-derived mouse embryonic stem (ES) cells by electroporation (BioRad Gene Pulsar at 230V, 500 μF capacitance), and the cells seeded and selected on feeder layers of irradiated fibroblasts in the presence of 350 μg/mL G418 and 0.2 μM FIAU. After 9 days, 100-500 resistant clones were picked and expanded.

A portion of each expanded clone was harvested and frozen for future use, while each remaining portion was genotyped. Briefly, DNA extracted from the cells was digested with BamHI, run on 0.8% agarose gel, and transferred to Hybond (Amersham) membranes. The membranes were prehybridized for 1 hour at 65° C. in RapidHyb and then hybridized overnight at 65° C. in the same solution containing $^{32}$P-labeled 3' probe (gray bar in FIG. 1). The prehybridized membranes were washed at 65° C. in 1×SSC/0.1% SDS, 0.3×SSC/0.1% SDS, and 0.1% SSC/0.1% SDS and then exposed to film. DNA from control, untransfected cells exhibited a single 15 kb band, heterozygous cells exhibited both 15 kb and 2.6 kb bands, and homozygous mutant cells exhibited a single 2.6 kb band.

After genotyping, four independent homozygous mutant clones were expanded, harvested, and then microinjected into blastocysts of C57BL/6 mice. The injected blastocysts were transferred into the uterine horn of surrogate mothers to generate chimera mice. Male chimeras from three (designated E3, E7, and D10) of the four clones were then cross-bred with C57BL/6 females and germ-line transmission was obtained for all three. Mice heterozygous for the PAPP-A nucleic acid construct were identified by genomic Southern blotting of tail tip DNA (as described above). Identified heterozygous mice were bred and crossed to produce progeny. Each progeny was genotyped using tail tip DNA and the Southern analysis technique described above. Wild-type mice have a single 15 kb band, heterozygous mice have both 15 kb and 2.6 kb bands, and homozygous mutants have a single 2.6 kb band.

Figure 2:
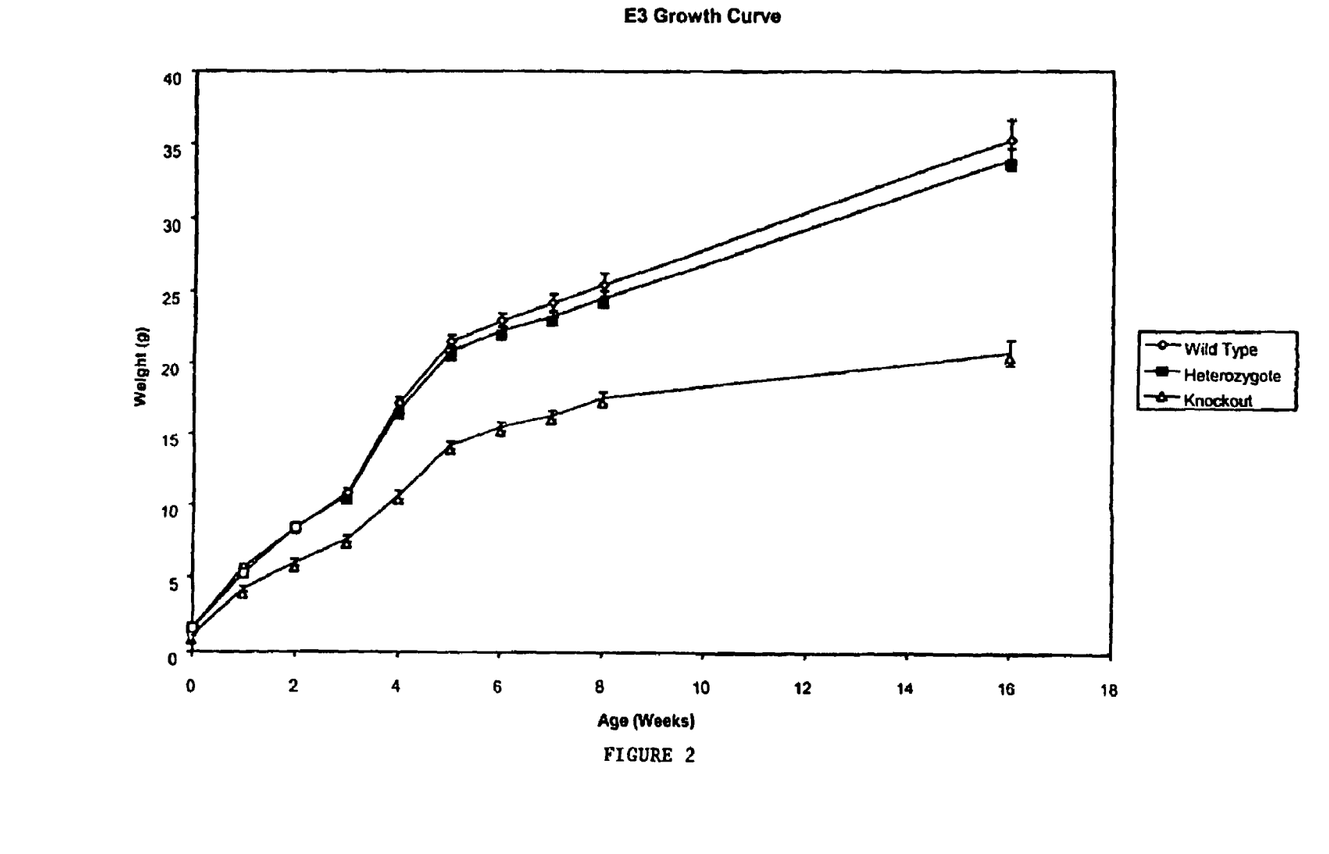
FIG. 2 is a graph depicting average body weights of wild type (diamonds), heterozygous PAPP-A disrupted (squares), and homozygous PAPP-A disrupted (triangles) mice as a function of age. Values are mean ±SEM of 20-100 animals.

The targeted allele segregated in a Mendelian fashion in PAPP-A heterozygous crosses. Of 170 F1 progeny analyzed, 38 (22%) were wild-type, 89 (53%) were heterozygous, and 43 (25%) were homozygous for the disrupted allele. The male:female ratio for homozygous mutants was approximately 50:50. Homozygous PAPP-A-deficient mice were 40% smaller than their wild-type littermates at birth [1.02±0.048 g PAPP-A(−/−) versus 1.68±0.047 g wild-type, n=20 each group]. This growth-deficient phenotype was the same in three independently targeted mouse lines. This size difference was maintained throughout postnatal growth (FIG. 2). At 18 months, wild-type mice weighed 50.5±3.73 g (n=4) and PAPP-A(−/−) mice weighed 28.6±2.60 g (n=10). At 16 weeks, circulating levels of IGF-I were 50% of the levels of IGF-I in wild-type littermates. Apart from their small size, the PAPP-A-deficient mice appear normal and reach sexual maturity. Both male and female homozygous mutant mice are fertile and produce viable offspring. The proportional dwarf phenotype of the PAPP-A-deficient mouse with retained fertility is like that of the IGF-II-deficient mouse. DeChiara, T. M., et al., *Nature* 345, 78-80 (1990).

To confirm that the targeted PAPP-A gene represented a null allele, primary mouse embryo fibroblasts (MEF) derived from E13.5 wild-type and homozygous PAPP-A mutant littermates were cultured and the conditioned media assayed for the presence of functional PAPP-A, i.e., IGFBP-4 protease activity. Cells at passage 2 were washed and changed to serum-free medium. After 24 h, conditioned medium was collected for cell-free assay. $^{125}$I-IGFBP-4 was incubated in the cell-conditioned medium without or with IGF-II for 6 h as previously described. See, Lawrence, J. B., et al. *Proc. Natl. Acad. Sci. USA* 96, 3149-3153 (1999); Boldt, H. B., et al. *Biochem. J.* 358, 359-367 (2001); and Conover, C. A., et al. *J. Biol. Chem.* 270, 4395-4400 (1995). Reaction products were analyzed by SDS-PAGE and autoradiography. $^{125}$I-IGFBP-4 incubated with wild-type MEF conditioned medium was proteolyzed into radiolabeled fragments of 18- and 14-kD, similar to the cleavage pattern produced by recombinant PAPP-A in the presence of IGF-II. Overgaard, M. T., et al. *J. Biol. Chem.* 275, 31128-31133 (2000). IGF-II is a cofactor for the proteolytic activity in vitro due to its ability to bind IGFBP-4 and increase susceptibility to PAPP-A (Qin, X., et al., *Arch. Biochem. Biophys.* 379, 209-216 (2000)), and fetal mouse fibroblasts secrete high levels of IGF-II (Adams, S. O., et al., *Nature* 302, 150-153 (1983)) sufficient to initiate PAPP-A mediated IGFBP-4 proteolysis in these cultures. In contrast, medium conditioned by MEF from PAPP-A(−/−) embryos exhibited no proteolysis of $^{125}$I-IGFBP-4 without or with addition of IGF-II. RNA prepared from neonatal tissues also indicated complete loss of PAPP-A expression by RT-PCR in homozygous mutants.

Whole embryo in situ hybridization indicated the presence of PAPP-A transcripts in wild-type mice at all embryonic stages investigated (E8.5-E15.5). PAPP-A was expressed in the paraxial mesoderm in the presomitic cells and in the posterior part of the somites, a pattern seen clearly from E9.5 to E13.5. In the limbs, PAPP-A expression was first detected in the forelimb at E10.5 as a diffuse expression in the center of the limb bud. At E11.5 there was a clear pattern in both forelimb and hindlimb. As the limb develops, the pattern in the limbs changes in a way that suggests the expression to be in pre-cartilage cells. At E10.5, defined PAPP-A expression can be seen in the brain. The staining seen in the region behind the ear and on the side appeared to be neural crest cells. There also was expression of PAPP-A on the distal part of the branchial arches.

PAPP-A expression in the mouse embryo parallels that of IGF-II, which was expressed in the head mesenchyme formed from both the mesoderm and cephalic portion of the neural crest, and in most mesoderm-derived tissues, particularly somites and lateral mesoderm. In addition, IGF-II expression in chondrocytes has been shown to be elevated prior to ossification. There appeared to be no difference in the level or pattern of IGF-II expression between wild-type and PAPP-A (−/−) mice. However, delays in limb and tail development were apparent in E12.5 PAPP-A(−/−) embryos. Most mesodermally-derived tissues of wild-type and PAPP-A(−/−) embryos also expressed IGFBP-4. This pattern of IGFBP-4 expression was consistent with previous studies. Similarly, Northern analysis for IGF-II and IGFBP-4 mRNA showed no difference of expression between wild-type and PAPP-A-null mouse embryos.

To determine if fibroblasts from PAPP-A-null embryos were responsive to IGF-I and -II, ten separate MEF cultures [5 wild-type, 5 PAPP-A(−/−) assayed in triplicate] were treated with 2, 5, or 10 nM of IGF-I and IGF-II, and 3H-thymidine incorporation determined as described previously. Conover, C. A., et al. *J. Biol. Chem.* 270, 4395-4400 (1995). Data are presented in Table 1 (mean ±SEM, n=5) and are expressed as percent of Control, i.e., no IGF. Fibroblasts from PAPP-A-null E13.5 embryos were as responsive as those from wild-type embryos to growth stimulation by IGF-I and -II, indicating that type IIGF receptor signaling was not impaired in the absence of PAPP-A gene expression. Thus, there was no apparent compensation in relevant components of the IGF system in the PAPP-A(−/−) mice.

TABLE 1

IGF stimulation of $^3$H-thymidine incorporation in mouse embryonic fibroblasts

| | | % of Control | |
|---|---|---|---|
| | | Wild-type | PAPP-A(−/−) |
| IGF-I | 2 nM | 162 ± 28 | 139 ± 17 |
| | 5 nM | 191 ± 18 | 196 ± 21 |
| | 10 nM | 224 ± 17 | 264 ± 13 |
| IGF-II | 2 nM | 154 ± 22 | 144 ± 36 |
| | 5 nM | 206 ± 37 | 200 ± 27 |
| | 10 nM | 227 ± 41 | 256 ± 20 |

The effect of PAPP-A gene deletion on bone development during embryogenesis was determined. Embryos were skinned, eviscerated and fixed in ethanol and then stained with alcian blue 8GS (cartilaginous elements) and alizarin red S (mineralized elements). Tissues were cleared with 1% KOH, and the skeletons stored in glycerol. Bone development in the PAPP-A(−/−) mice was similar to that of the IGF-II gene mutant (Liu, J.-P., et al. *Cell* 75, 59-72 (1993)) with developmental delay in the appearance of ossification centers in the clavicle, facial and cranial bones, vertebrae, and the digits of the forelimbs and hindlimbs. The initiation of mineralization occurs between E12.5 and E13.5 in the mouse. The first bone to mineralize in both wild-type and PAPP-A (−/−) mice was the clavicle. At E13.5, the middle portion of the clavicle was clearly mineralized in the wild-type, while mineralization was just initiated in PAPP-A(−/−) littermates. The delay in mineralization was approximately one day as estimated by review of several skeletons at E13.5, E14.5, E16.5, E18.5, and newborn. The delay in mineralization occurred both in bones that form via intramembranous ossification (cranial vault) and endochondral ossification (vertebrae, metatarsals). At E16.5, no caudal vertebrae were mineralized in the PAPP-A(−/−) mouse, while three to four caudal vertebral elements were undergoing mineralization in wild-type littermates. Likewise an additional metatarsal had initiated mineralization in the wild-type compared to the PAPP-A(−/−) mice. The frontals and parietals bones of the cranial vault are both undergoing mineralization at E16.5, but these processes are far less complete in PAPP-A(−/−).

Body size of mammals involves interaction of multiple genetic modifiers that coordinate cell proliferation, cell death, and differentiation in relation to location, timing, and duration in early embryogenesis. PAPP-A can now be considered one of these growth determinants. The results of this study demonstrate a causal relationship between deletion of the PAPP-A gene in mice and a growth-deficient phenotype that becomes apparent at least as early as embryonic day 12.5 and persists after birth. Although PAPP-A-deficient mice were significantly smaller than wild-type littermates, their proportions were constant, indicating that the presence of PAPP-A is necessary for an optimal fetal growth program. These findings, together with the finding of proportional reduction in tissue weights (Table 2), indicate that the impact of PAPP-A gene mutation on embryonic growth occurred prior to organogenesis (E10-14 in the mouse).

TABLE 2

Allometric measurements

|  | Wild-Type | PAPP-A(−/−) | % | P-Value |
|---|---|---|---|---|
| Body weight (g) | 33.7 ± 1.5 | 18.0 ± 0.9 | 53 | <0.0001 |
| Heart (g) | 0.176 ± 0.0075 | 0.107 ± 0.0058 | 61 | <0.0001 |
| Spleen (g) | 0.093 ± 0.0067 | 0.040 ± 0.0033 | 43 | <0.0001 |
| Liver (g) | 1.674 ± 0.093 | 0.922 ± 0.084 | 55 | <0.0001 |
| Kidney (g) | 0.208 ± 0.008 | 0.121 ± 0.009 | 58 | <0.0001 |

Body and tissue weights (mean ± SEM) of 6 wild-type and 6 PAPP-A(−/−) male mice at 8 weeks.
%, percent of PAPP-A(−/−) weight compared to wild-type weight.

The principal period of IGF-II impact on body size has been shown to occur specifically during E9-E10. Burns, J. L. and Hassan, A. B. *Development* 128, 3819-3830 (2001). In the absence of the IGF-II gene, there are significant decreases in cell proliferation and cell survival over this window of time that account for the smaller size of the embryo, detected at ~E12.5. Considering that IGFBP-4 is expressed and present during embryonic development and can inhibit IGF-II action through sequestration, the absence of PAPP-A for amplification of receptor-mediated IGF-II signaling during E9-10 could result in altered fetal growth. Decreased size of PAPP-A(−/−) mice likely is due to deficit of anabolic signaling of endogenous IGF-II during a critical time early in fetal development in the mouse that determines organ and body size.

Example 2

Increasing Lifespan

Figure 3:
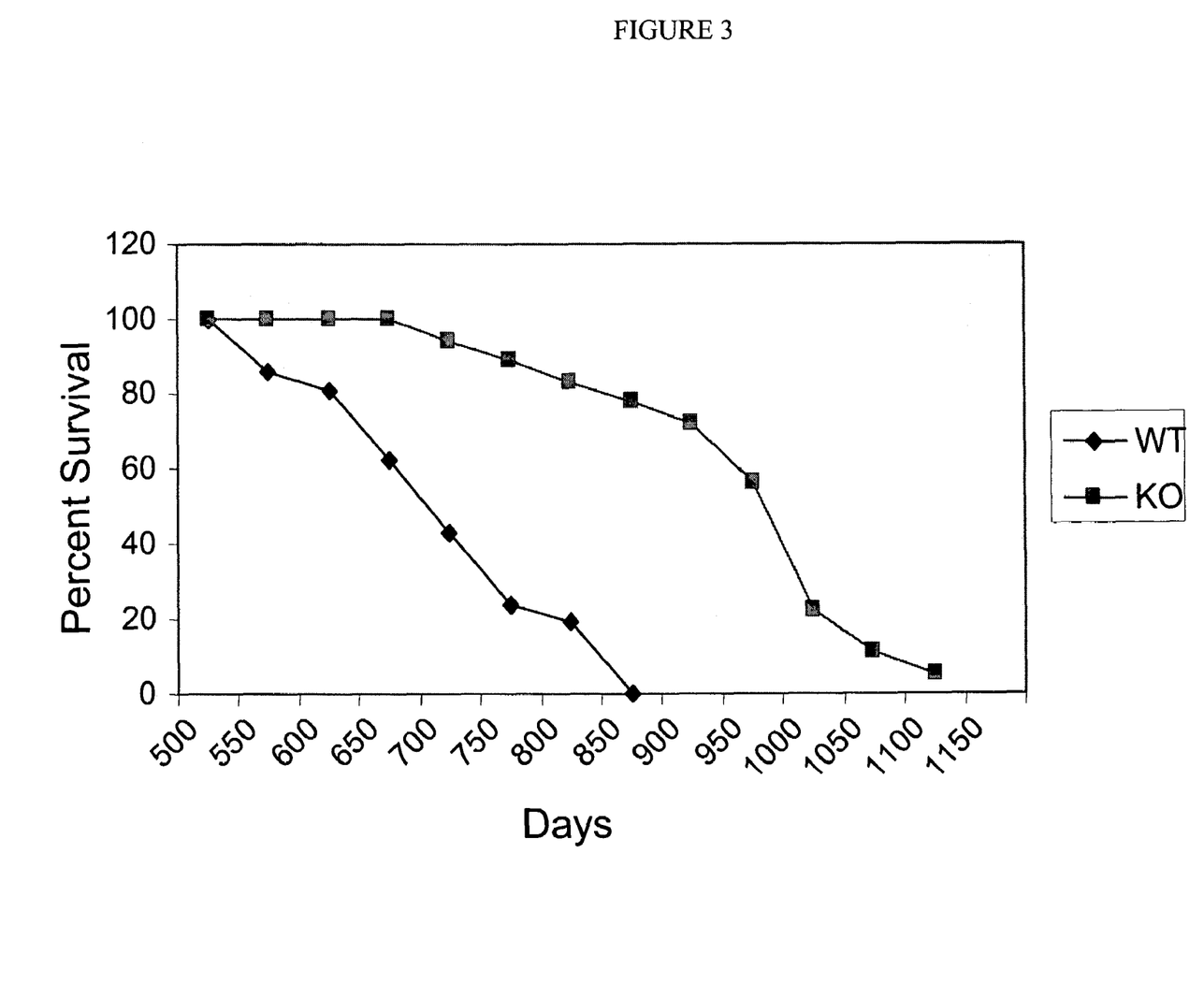
FIG. 3 is a graph plotting percent of surviving mice versus time for wild-type (WT) and homozygous PAPP-A disrupted (KO) mice.

To confirm that PAPP-A polypeptide activity is involved in the aging process of mammals, the following experiment was conducted. Survival distribution of 46 PAPP-A knock-out and wild-type siblings from heterozygous matings was determined. Loss of PAPP-A expression resulted in the extension of mean lifetime survival of mice by 38 percent (960+28 days versus 698+23 days, P <0.0001; FIG. 3). These results were from pooled males and females, but separation by sex revealed significant increases in lifespan for both males (33 percent) and females (41 percent). Maximum lifespan measured as the average age of the last decile of surviving mice, was 872 days for wild-type and 1134 days for PAPP-A (−/−) mice. The increase in lifespan was not associated with alterations in serum glucose, insulin, IGF-I or growth hormone levels. In addition, dietary intake was not significantly different between PAPP-A (−/−) knock-out and wild-type mice. Thus, the longevity of these animals does not appear to be attributed to caloric restriction, growth hormone abnormalities, or lowered circulating IGF-I levels. Pathology on a limited group of 22- to 28-month-old animals revealed extensive tumors (e.g., liver, lung, kidney, and colon tumors) and enlarged spleen and lymph nodes in 7 of 9 wild-type mice compared to small numbers and sizes of tumors (e.g., liver and lung tumors) in only 2 of 7 PAPP-A (−/−) knock-out mice. None of the PAPP-A (−/−) knock-out mice had obvious spleen or lymph node abnormalities. In preliminary studies, PAPP-A (−/−) knock-out mice were found to be resistant to the development of experimentally-induced neointimal hyperplasia (Resch et al., *Proceedings of the 85th Annual Meeting of the Endocrine Society*, Abstract 852806 (2003)) and atherosclerosis.

These results indicate that the PAPP-A (−/−) knock-out mouse can be used as a model for investigating molecular issues of aging that relate to IGF-I signaling and point to PAPP-A as a target with potential to regulate longevity and age-related diseases by moderate restraint of IGF signaling. These results also confirm that reducing PAPP-A polypeptide activity in a mammal can increase the mammal's lifespan.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying a compound having the ability to increase the average lifespan of a population of mice, said method comprising:
    (a) administering a test compound having the ability to reduce PAPP-A polypeptide activity to a population of mammals, and
    (b) determining whether or not said population has a longer average lifespan than the average lifespan of a control population not administered said test compound, wherein the presence of said longer average lifespan indicates that said test compound is said compound having the potential ability to increase the average lifespan of said population of mice.

2. The method of claim 1, wherein said test compound is an siRNA molecule.

3. The method of claim 1, wherein said method further comprises comparing the average lifespan of said population of mice to the average lifespan of a positive control population of PAPP-A knock-out mice to confirm the identification of a compound having the ability to increase the average lifespan of a mouse.

4. The method of claim 1, wherein said method comprises determining whether or not said population has at least a 10 percent longer average lifespan than the average lifespan of a control population not administered said test compound.

5. The method of claim 1, wherein said method comprises determining whether or not said population has at least a 30 percent longer average lifespan than the average lifespan of a control population not administered said test compound.

6. The method of claim 1, wherein said method comprises determining whether or not said population has at least a 40 percent longer average lifespan than the average lifespan of a control population not administered said test compound.

7. The method of claim 1, wherein said method comprises determining whether or not said population has a 30 to 40 percent longer average lifespan than the average lifespan of a control population not administered said test compound.

* * * * *